United States Patent [19]

Leuchtenberger et al.

[11] Patent Number: 5,416,019

[45] Date of Patent: May 16, 1995

[54] RHODOCOCCUS MICROORGANISMS THAT PRODUCE PHENYLALANINE DEHYDROGANASE

[75] Inventors: Wolfgang Leuchtenberger, Bruchköbel; Maria-Regina Kula, Wolfenbüttel; Werner Hummel, Braunschweig; Horst Schütte, Salzgitter, all of Germany

[73] Assignee: Degussa Aktiengesellschaft, Frankfurt am Main, Germany

[21] Appl. No.: 186,501

[22] Filed: Jan. 26, 1994

Related U.S. Application Data

[60] Continuation of Ser. No. 897,484, Jun. 12, 1992, abandoned, which is a division of Ser. No. 545,144, Jun. 28, 1990, abandoned, which is a continuation of Ser. No. 380,750, Jul. 17, 1989, abandoned, which is a continuation of Ser. No. 808,835, Dec. 12, 1985, abandoned.

[30] Foreign Application Priority Data

Dec. 19, 1984 [DE] Germany .................... 34 46 304.6

[51] Int. Cl.⁶ .............................................. C12N 1/20
[52] U.S. Cl. ................................ 435/252.1; 435/253.2; 435/108
[58] Field of Search ............ 435/253.2, 252.32, 252.1, 435/172.1, 34, 189, 190, 108

[56] References Cited

U.S. PATENT DOCUMENTS 4,590,161  5/1986  Kula et al. .......................... 435/108

OTHER PUBLICATIONS

Goodfellow et al, "The Biology of Actinomycetes", 1985, pp. 91–94.
Hummel et al, Appl. Microbial Biotechnol., 1987, 26:409–416.
Bergey's Manual, 1974, p. 743.
Rast et al, FFMS Microbiol. Lett. vol. 7, 1980 pp. 1–6.

*Primary Examiner*—Irene Marx
*Attorney, Agent, or Firm*—Cushman, Darby & Cushman

[57] ABSTRACT

The invention is directed to obtaining phenylalanine-dehydrogenase containing microorganisms by a special selection process comprising obtaining microorganisms, especially strains of Rhodococcus and the phenylalanine-dehydrogenase obtained in them. With the help of this enzyme there are obtained L-α-aminoacids from the corresponding ketocarboxylic acids by reductive amination.

2 Claims, 2 Drawing Sheets

Fig. 1. PHENYLALANINE DEHYDROGENASE (M4) pH DEPENDENCY OF THE REVERSIBLE REACTION

RHODOCOCCUS MICROORGANISMS THAT PRODUCE PHENYLALANINE DEHYDROGANASE

This application is a continuation of application Ser. No. 07/897,484 filed Jun. 12, 1991, now abandoned, which is a division of application Ser. No. 07/545,144 filed Jun. 28, 1990, now abandoned, which is a continuation of application Ser. No. 06/380,750 filed Jul. 17, 1989, now abandoned, which continuation of application Ser. No. 06/808,835 filed Feb. 12, 1985, now abandoned.

BACKGROUND OF THE INVENTION

The invention is directed to a process for obtaining phenylalanine-dehydrogenase containing microorganisms, microorganisms which contain phenylalanine-dehydrogenase and their use for the production of L-α-aminocarboxylic acids.

The use of enzymes as catalysts has proven advantages in the sterospecific production of L-phenylalanine. It is known from German OS 3307095 to reductively aminate phenyl pyruvate with a phenylalanine-dehydrogenase and to obtain the corresponding enzyme from Brevibacterium spec. (DSM 2448). However, the thus isolated enzyme has been found to be relatively unstable.

Attempts to obtain additional microorganisms which contain phenylalanine-dehydrogenase with the help of the methods described there have not led to success.

This is founded on the fact that the nutrient medium known from German OS 3307095 makes possible an unspecific growth of different microorganisms, which naturally makes very difficult the selection of the desired strains.

The problem of the present invention was to develop a process for the isolation of phenylalanine-dehydrogenase containing microorganisms which make possible a quick selection of suitable strains and a stable phenylalanine-dehydrogenase.

SUMMARY OF THE INVENTION

The invention is directed to a process of obtaining phenylalanine-dehydrogenase containing microorganisms by aerobic cultivation of microorganism-containing samples in aqueous nutrient media which contain a source of carbon, nitrogen and mineral salts and thiamine, comprising first incubating the samples in a nutrient medium having an alkali propionate (e.g. sodium propionate or potassium propionate) content of 0.1–0.5 g/l, reinoculating the colony sample formed on a nutrient medium which contains an inductor, incubating and selecting the microorganisms which grow on both nutrient media.

As microorganism-containing samples for example, there are chosen soil samples which are made into a suspension with sterile salt solution (0.9% NaCl), diluted in conventional manner and aliquots are placed on petri dishes containing solid nutrient media. The nutrient medium, for example has the standard composition to which there has been added an alkali propionate, preferably sodium propionate according to the invention.

| | |
|---|---|
| Propionic acid, Na-salt | 0.01–0.05 g, preferably 0.2 g |
| $KNO_3$ | 0.01 g |
| $KH_2PO_4$ | 0.1 g |
| NaCl | 0.25 g |
| $MgSO_4.7H_2O$ | 100 mg |
| $CaCO_3$ | 20 mg |
| Trace element solution | 1 ml |
| Distilled water | 1 l |
| Agar | 20 g |
| pH-value | 6.5–7.5, preferably 7.0 |

The medium was sterilized by autoclaving, after cooling there was added 1 ml of sterile filtered vitamin-solution per 1 liter of medium as well as 50 mg cycloheximide (Actidone) per 1 liter (composition of the vitamin solution according to: H. G. Schlegel, "Allgemeine Mikrobiologie", Thieme Verlag, page 169 (1981) and the nutrient medium poured into sterile petri dishes.

The inoculated plates were incubated for 4–6 days, at 23 to 32° C., preferably at 27° C. After the growth of the microorganisms the colony samples were sterilely reinocculated from agar plates having a suitable number of colonies (50–200) onto a complete replica; the re-replicated on 2 plates which contain different agar nutrient mediums: One plate contains the above-mentioned propionate medium, the other a nutrient medium with L-phenylalanine as inductor and having, for example the following composition:

| (Phenylalanine-Medium): | |
|---|---|
| L-phenylalanine | 1 to 15 g, preferably 10 g/l |
| $KH_2PO_4$ | 2 g |
| Yeast extract | 0.2 g |
| Agar | 20 g |
| Distilled water | 1 l |
| The pH is between 6 to 8, preferably at 7.2 | |

The plates were again incubated 3–5 days at 23 to 32° C., preferably at 27° C. By comparison of the colony samples there can be found out which organisms can grow on both propionate and phenylalanine medium; these were inoculated and in the following procedures held on phenylalanine medium.

The isolated microorganisms were then in customary manner checked for purity (dilution streaking out, microscope), propagated at 23 to 32° C., preferably at 27° C. The fluid medium has the following composition:

| | |
|---|---|
| L-phenylalanine | 1 to 15 g, preferably 10 g |
| steeping corn liquor (dry powder) | 2 g |
| $KH_2PO_4$ | 2 g |
| Distilled water | 1 l |
| pH | 6 to 8, preferably 7.2 |

After 2 to 3 days the cells were sedimented and the enzyme obtained from the disintegrated microorganisms in known manner.

By this method of isolation it is possible in simple manner from the microorganism population of a soil sample to enrich and isolate those organisms which contain the desired phenylalanine-dehydrogenase activity. Thus, from 20 soil samples from the environs of Brunswick there could be obtained 7 isolates, which have Phe-DH-activity (Table 1). The isolated organisms can be divided into two groups:

5 isolates which belong to the genus Brevibacterium (each from a different soil sample) as well as 2 isolates which belong to the family Rhodococcus, as is shown by the following properties:

Growth in short, gram-positive rods, which convert with increasing age into cocci forms; cells are immobile and form no spores; strict aerobic growth; acid formation from glucose, catalase and nitrate reduction positive, urea splitting positive, gelatin, casein, and starch breakdown negative; H₂S formation negative; growth at 41° C. negative. The cell walls contain meso-diaminopimelic acid, there were detected as cell wall sugars arabinose and galactose. The menaquinone are of Type MK-8 (H₂). Both isolates contain tuberculostearic acid and mycolic acids having 30 to 50 carbon atoms. The fatty acids liberated by pyrolytic splitting of methyl esters of mycolic acids contain 12–18 carbon atoms. The color of the colonies of both isolates is saffron-yellow (Type 41 according to the RAL Color Code) (H. Seiler) *J. Gen. Microbiol,* Volume 129, pages 1433–1471 (1983). The organisms require thiamine for growth.

The isolates are an additional subject matter of the invention and were deposited at the DSM (German Collection of Microorganisms) on Sep. 7, 1984 as Rhodococcus spec. M4 under the number of 3041 and as Rhodococcus spec. I3 under the number 3040.

The microorganisms can be preserved as lyophilized cultures, by freezing at −80° C. or in liquid nitrogen at −196° C., working cultures were maintained on agar slant tubes (phenylalanine medium).

Both strains did not utilize the aminoacid D-phenylalanine.

(b) There is attained in growing on L-phenylalanine higher volume yields (20–25,000 U/l instead of 3–6,000 U/l);

(c) The enzymes are of clearly better stability.

The phenylalanine-dehydrogenase can be described enzymologically as follows:

(a) It catalyzes the reductive amination of aromatic α-ketocarboxylic acids, the systematic name is L-phenylalanine, AND⁺-oxidoreductase (desaminating), and it belongs in the E.C. Group 1.4.1;

(b) optimum pH of the reduction amination of phenylpyruvic acid is 9.3±1;

(c) optimum pH of the oxidative disamination of L-phenylalanine is 10.0±1;

(d) the $K_M$ value for NaDH amounts to 0.08 mM.

L-phenylalanine and L-phenylalanineamide are preferably employed as inductors; however, L-histidine is also suitable to a limited extent.

The phenylalanine-dehydrogenase is employed in the presence of ammonium ions and NADH as coenzyme to convert phenylpyruvic acid, p-hydroxyphenylpyruvic acid, indole pyruvic acid or 2-keto-4-methylmercaptobutyric acid into the corresponding L-α-aminocarboxylic acids.

The process is preferably carried out at 20 to 30° C. and a pH of 8.5 to 10.

Advantageous the operation is performed under coenzyme-regeneration as is known from German OS 3307095 and the related Kula U.S. application Ser. No. 583,325 of Feb. 24, 1984.

TABLE 1

Characterization Of The Isolate

| Designation of the Isolate | Source of the Nutrient Sample | Family of the Isolate | PheDH Spec. Act. (U/mg) | Volume Act. (U/l) | Remaining Stability (1% Activity after 4 days (4° C.) |
|---|---|---|---|---|---|
| | Silt from the Shore | | | | |
| M4 | "Ententeich" | Rhodococcus | 16 | 13,000 | 90% |
| I3 | Ribbesbuttel Cornfield | Rhodococcus | 11 | 8,600 | 44% |
| I2 | Ribbesbuttel Cornfield | Brevibacterium | 1.5 | 640 | 0% |
| IV/6 | Entrance GBF, Turf | Brevibacterium | 1.0 | 520 | 0% |
| V/II | Compost earth | Brevibacterium | 0.5 | 205 | 0% |
| VI/4 | Turf, Stockheim (Matthiesen) | Brevibacterium | 0.1 | 133 | 0% |
| T2 | Parking place Zimmerstrasse | Brevibacterium | 0.7 | 840 | 0% |

Preliminary experiments with crude extractenzyme preparations have shown that phenylalanine-dehydrogenase from the individual isolates of the genus Brevibacterium are comparable with the enzyme described in German OS 3307095.4 (and related Kula U.S. application Ser. No. 583,325, filed Feb. 4, 1984, the entire disclosure of which is hereby incorporated by reference and relied upon) in regard to the specific enzyme activity, volume yield, inductability and stability.

The enzymes from both of the isolates of the genus Rhodococcus in comparison thereto demonstrate as clear superiority:

(a) The enzyme in the crude extract shows higher specific activities (20–30 U/mg) protein instead of 2–5 U/mg);

In an analogous manner there can also be used non-disintegrated bacteria cells.

The enzyme is also suited to determine in an enzymatic manner in aqueous solutions the concentration of the above mentioned α-ketocarboxylic acids or aminoacids.

After identification of the isolate known strains of the genus Rhodococcus from the stock collection (Deutsche Sammlung yon Mikroorganismen, Gottingen) (German Collection of Microorganisms) were tested as to phenylalanine-dehydrogenase activity. At present there are known 11 types of this genus (M. Goodfellow and D. E., Minnikin in: *The Prokaryates* (M. P. Starr et al editors), pages 2016–2029, Springer Verlag, Berlin, Heidelberg, New York (1981); M. Goodfellow System, *Appl. Microbiol,* Volume 5, pages 225–229 (1984); in each case the standard strain was grown in MP-medium (1% L-phenylalanine, 0.2% corn steep water, 0.2%

KH$_2$PO$_4$). After 40 hours growth at 27° C. the cells were disintegrated and the activity of the phenylalanine-dehydrogenase in the crude extract determined.

It was found that only the strains of *Rhodococcus erythropolis* (DSM 43066 and 743) utilized L-phenylalanine (OD$_{578}$ 28.0 for 43066 and OD 15.3 for 743) and had phenylalanine-dehydrogenase activity (12600 U/l for 43066 and 1031 U/l for 743), which, however, are clearly below those of the new Rhodococcus.

Larger amounts of phenylalanine-dehydrogenase can be obtained from Rhodococus spec. M4 and I3 by growing the microorganisms in known manner in a bioreactor on the desired scale and the enzyme isolated therefrom.

The following preferred conditions apply for a successful cultivation:

(a) a good aeration (obligatory on aerobic organisms);
(b) a starting pH of 6.0–8.0;
(c) the presence of mineral salts (e.g. in complex form as corn steep water);
(d) the presence of small amounts of thiamine (1–2 g/l);
(e) an L-phenylalanine content of 0.5–1.5% in the medium for induction of the PheDH;
(f) a temperature of 23 to 32° C.

In the samples there were measured:

(a) the optical density (turbidity) of the culture at 578 nm as a measure for the growth;
(b) the phenylalanine content in the medium (after centrifuging off the cells) with the help of an aminoacid analyzer;
(c) the enzyme content using a photometric test. The test mixture contains 0.7M ammonium chloride-/ammonium buffer pH 8.5, 0.1 mM NADH, 10 mM phenyl pyruvic acid and limited amounts of enzyme (1–20 g protein per test). The decrease of the extinction of NADH at 340 nm was measured. A zero value was plotted from the obtained values, which was obtained by running the test without addition of phenyl pyruvic acid. The enzyme activity was stated in international units, whereby one Unit signifies the dropping of 1 Mol NADH/min.

For industrial employment the cells obtained by cultivation can be used directly or the enzyme contained in the cells isolated and then be employed in the cell-free system. The isolation of enzyme is possible after disintegration of the cells by combination of known methods for the First there is set free the contents from the bacterial wet mass, preferably by a mechanical disintegration of the cells, for example with the help of a glass bead mill, a high pressure homogenizer of a supersonic treatment.

In a second step the broken pieces of the cell are separated off according to German patent 2639129 from the crude extract via an aqueous two phase system.

The upper phase contains practically the entire activity of L-phenylalanine, dehydrogenase and is subjected further to a dialysis process.

The dialyzed enzyme was subsequently further purified with the help of DEAE-cellulose-chromatography and then there was attained the desired degree of purification after carrying out Interfacial Salting Out- Chromatography, for example on Sepharose 4B.

The process can comprise, consist essentially of, or consist of the recited steps with the stated materials.

DETAILED DESCRIPTION

EXAMPLE 1

Production of the Phenylalanine-Dehydrogenase

For the cultivation there was used a 2 liter bioreactor which was filled with 1.5 liters of medium. The medium contained per liter 10 grams of L-phenylalanine; 2 grams of KH$_2$PO$_4$; 2 grams corn steep water (as a dry powder); the pH was 7.0.

After sterilization the medium was inoculated with 50 ml of a preculture, which was grown for 48 hours in the same medium. The growth conditions in the fermenter were:

Temperature: 27° C.
Aeration rate: 60 liters of air per hour
Turbine stirrer at 4/0 rpm.

At various times of the growth samples (40 ml) were withdrawn and after a test for enzyme activity the maximum attainable enzyme content respectively the most favorable harvesting time determined.

Figure 2:
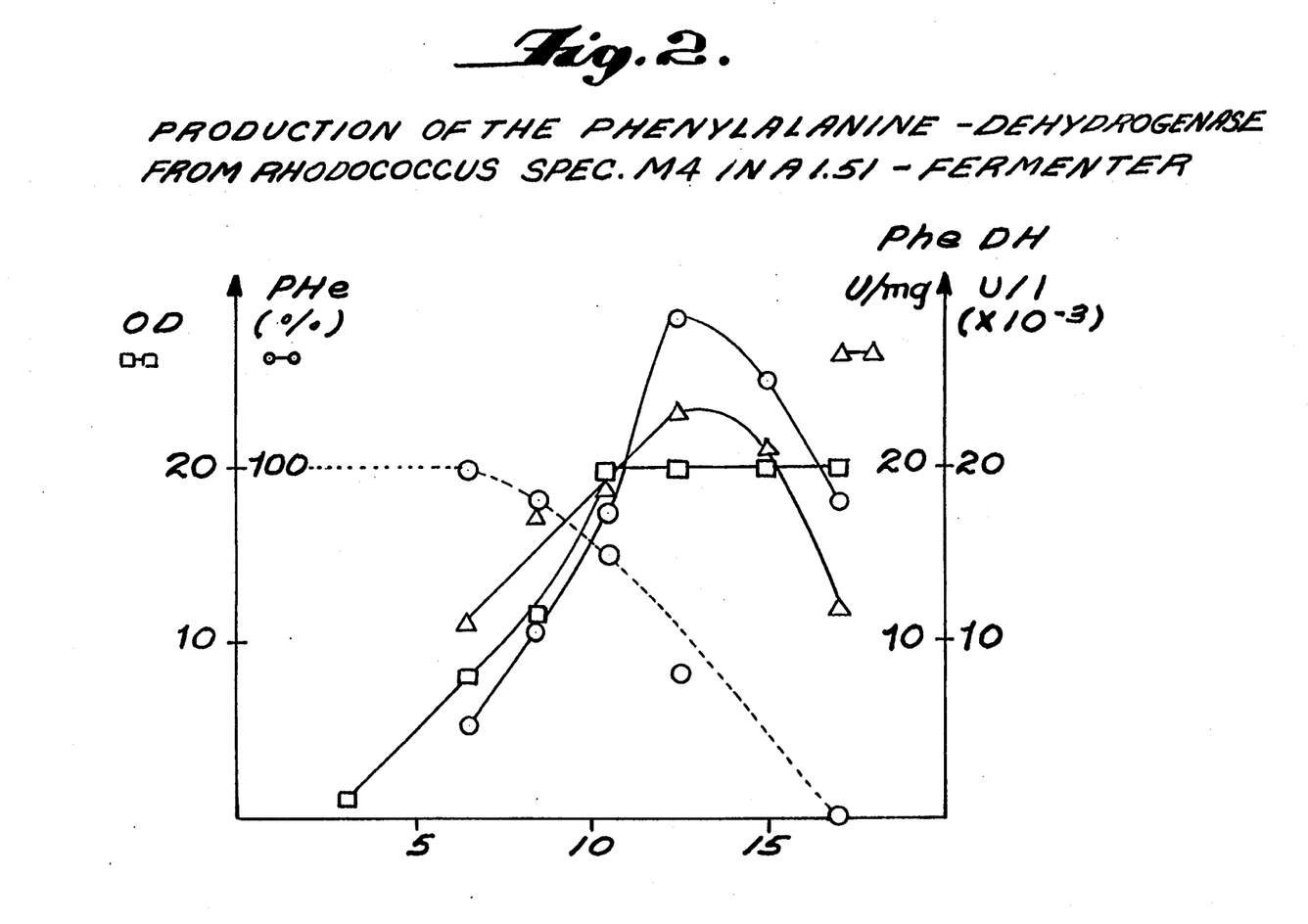
FIG. 2 is a graph showing the production of phenylalanine-dehydrogenase from Rhodococcus spec. M4 in a 1.5l fermenter.

FIG. 2 shows that the enzyme is formed in an early growth phase; the enzyme content increases especially when the organism commences to breakdown phenylalanine. Enzyme contents clearly above 20,000 units per liter of medium can be attained at this point. In the further course of the growth the enzyme content is reduced again.

After centrifuging off the bacteria there is obtained from a 1.5 liter fermentation 70 grams of cells (wet mass) having a total enzyme activity of 22,000 units.

EXAMPLE 2

Formation Of The PheDH Depending On The Aminoacid In The Medium

Strain M4 was cultivated in a medium containing 0.2% corn steep water (dry powder), 0.2% KH$_2$PO$_4$ and in each case 1% of an aminoacid; the pH before the beginning of the cultivation was 7.4. In each case there was inoculated 100 ml of medium; after 40 hours growth the cells were centrifuged off and after disintegration of the cells with glass beads the activity of the PheDH determined. Table 2 shows that the addition of L-phenylalanine is necessary for a good yield of enzyme, other natural aminoacids result in slight (histidine) or no (isoleucine) content of enzyme. L-phenylalanine can be replaced as inductor by the derivative L-phenylalanineamide. The strain M4 cannot grow on several natural aminoacids (e.g. L-tryptophane, L-tyrosine, L-alanine, or L-glutamic acid). Likewise, in contrast to Brevibacterium spec. (DSM 2448) strain M4 does not utilize the aminoacid D-phenylalanine.

TABLE 2

| Aminoacid | OD$_{578}$ | U/mg | U/l |
| --- | --- | --- | --- |
| L-phenylalanine | 31 | 7.25 | 15,200 |
| L-histidine | 4 | 1.81 | 820 |
| L-phenylalanineamide | 8 | 8.49 | 3,550 |
| L-isoleucine | 14 | 0 | 0 |

TABLE 2-continued

| Aminoacid | OD₅₇₈ | U/mg | U/l |
|---|---|---|---|
| D-phenylalanine | 0 | | |

EXAMPLE 3

Formation Of The PheDH Depending On The Concentration In The Medium

Strain M4 was cultivated in a medium containing 0.2% corn steep water (dry powder), 0.2% $KH_2PO_4$ and increasing amounts of L-phenylalanine (up to 1.5%); the pH before the beginning of the cultivation was 7.4.

In each case 100 ml of medium was inoculated; after 40 hours growth the cells were centrifuged off and after disintegration of the cells with glass beads the activity of the PheDH was determined. Table 3 shows that by increasing the phenylalanine content in the medium the yield of enzyme also can be increased, with 1.5% phenylalanine thus there can be obtained about 26,000 U (units) per 1 liter of medium. The course of the specific enzyme activity (U/mg) besides shows that a content of phenylalanine above 0.5% is preferred.

TABLE 3

| L-Phe gl/ | Phenylalanine-Dehydrogenase U/mg | U/l |
|---|---|---|
| 1 | 0 | 0 |
| 2 | 0 | 0 |
| 5 | 1 | 2000 |
| 8 | 12.1 | 14000 |
| 10 | 14.6 | 18000 |
| 12 | 16.6 | 23000 |
| 15 | 20.4 | 26000 |

EXAMPLE 4

Dependence Of The Rate Of Reaction On The pH (a) Reduction Amination

The rate of reaction of the reduction amination of phenyl pyruvic acid to L-phenylalanine was investigated as to dependency on the pH of the reaction solution. The test mixture had the following composition:

0.25 mM NADH, 1.5 mM phenyl pyruvic acid and limiting amounts of an enzyme in a 0.7 M ammonium chloride solution at different pH values. Different pH values were established by addition of ammonia or hydrochloric acid to the 0.7M ammonium chloride solution before mixing together the test mixture.

Figure 1:
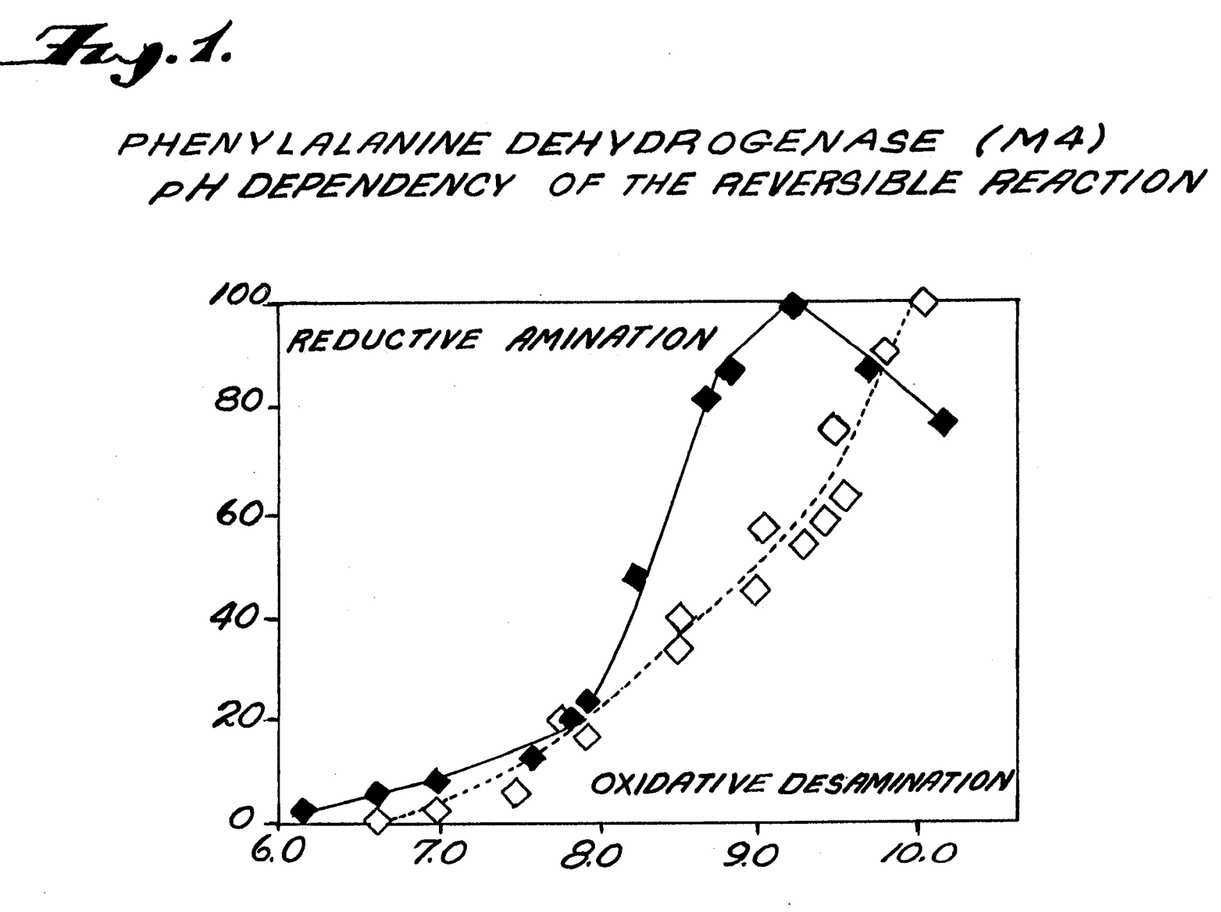
FIG. 1 is a graph showing pH dependency of the reversible reductive amination-oxidation desamination reaction.

In FIG. 1 there is plotted the rate of reaction as a function of the pH in the region of 6.0 to 10.2. The pH optimum is 9.25. The pH was measured in the reaction mixture.

(b) Oxidative Desamination

The rate of reaction of the oxidative desamination of L-phenylalanine, catalyzed by the L-phenylalanine-dehydrogenase was likewise investigated as to dependency on pH. The test mixture had the following composition 3 mM $NAD^+$ and 6 mM L-phenylalanine in a 0.1M glycine/NaCl/NaOH buffer at different pH values. There was established different pH values by addition of hydrochloric acid or sodium hydroxide solution to the buffer before mixing together the test mixture. The results are likewise collected in FIG. 1 for the range of pH 6.5 to 10.1. The reverse reaction increases up to pH 10.1. The pH was measured in the reaction mixture.

EXAMPLE 5

Dependency Of The Rate Of Reaction On The Substrate Concentrations

Reductive Amination (a) The dependency of the rate of reaction of the reductive amination of phenyl pyruvic acid to L-phenylalanine for the substrate NaDH was investigated in the following test mixtures:

0.7M ammonium chloride/ammonia buffer (pH 9.5),1.5 mM phenyl pyruvic acid, limiting amounts of enzyme. The NADH concentration in the test mixture was varied in the range of 0.025–0.3 mM.

It was shown that the optimum speed of reaction was reached at 0.25 mM. The value for NADH is 0.08 mM.

(b) The reductive amination of different α-ketocarboxylic acids was investigated as to the dependency on the ketoacid concentration. For this purpose the following test mixtures were used.

0.7M ammonium chloride/ammonia buffer (pH 9.5), 0.25 mM NADH, limiting amounts of enzyme. The ketocarboxylic acid concentration was varied in each case in the range of 0.01 to 3 mM.

The beginning speed of reaction (change in extinction 340 nm/minute) was evaluated according Michaelis-Mentens. The $K_M$ and $V_{max}$ values found are collected in Table 4. Because of the disturbances of the optical test in the case of the substrate indole pyruvic acid and p-hydroxyphenyl pyruvic acid the reductive amination to L-tyrptophane or tyrosine as function of the time on the aminoacid analyzer was determined (Biotronik BC 6000, equipped with an Integrator Biotronik, System 1, in a 1-column program; as reference solution there was used an aminoacid-Standard IV of the Pierce company.

Oxidative Desamination (a) The dependency of the speed of reaction of the oxidative desamination of L-phenylalanine on the $NAD^+$ concentration was investigated in the following test mixture.

0.1 M glycine-NaCl/NaOH buffer (pH 10.7, 4 mM L-phenylalanine, limiting amounts of enzyme. The $NAD^+$ concentration was varied in the range of 0.1 to 5.0 mM. It showed that the optimum reaction was reached at a concentration of 3 mM.

(b) The dependency of the speed of reaction of the oxidative desamination of the L-aminoacid concentration was investigated in the following test mixtures:

0.1 M glycine-NaCl/NaOH buffer (pH 10.7), 3 mM NAD, limiting amounts of enzyme. The L-aminoacid concentration was varied in the range of 0.3 to 15 mM.

The $K_m$ value for L-phenylalanine was 0.8 mM; the corresponding values for the other aminoacids are collected in Table 5.

TABLE 4

Substrate Specificity For The Reductive Amination Of The Phenylalanine-Dehydrogenase

| Substrate | $V_{max}$ (Relative To Phenyl Pyruvic Acid) | $K_M^*$ [M] |
|---|---|---|
| Phenyl pyruvic acid | 100 | $1.6 \cdot 10^{-4}$ |
| p-Hydroxyphenylpyruvic | 5 | $2.4 \cdot 10^{-3}$ |
| Indole pyruvic acid | 3 | $7.7 \cdot 10^{-3}$ |

TABLE 4-continued

Substrate Specificity For The Reductive
Amination Of The Phenylalanine-Dehydrogenase

| Substrate | $V_{max}$ (Relative To Phenyl Pyruvic Acid) | $K_M$* [M] |
|---|---|---|
| 2-Keto-4-methyl-mercapto butyrate | 33 | $2.1 \cdot 10^{-3}$ |
| NADH | | $8 \cdot 10^{-5}$ |

TABLE 5

Substrate Specificity For The Oxidative
Desaminaton Of The Phenylalanine-Dehydrogenase

| Substrate | $V_{max}$ (Relative To L-Phenylalanine) | $K_M$* M |
|---|---|---|
| L-Phenylalanine | 100 | $7.5 \cdot 10^{-4}$ |
| L-Tryptophane | 2 | $1.05 \cdot 10^{-2}$ |
| L-Methionine | 4 | $4.3 \cdot 10^{-3}$ |
| NAD+ | | $2.2 \cdot 10^{-4}$ |

*$K_M$: Michaelis-constant (D. Burk, T. Amer. Chem. Soc. 56(1934)658)

EXAMPLE 6

Stability Of The PheDH

Strain M4 was cultivated in 100 ml of the following composition:

0.2% corn steep water (dry powder), 0.2% KH2PO4, 1% L-Phe, pH was 7.0. After 40 hours incubation at 27° C. on the round shaking machine the cells were harvested by centrifugation, disisintegrated by glass beads and the cell supernatant obtained by centrifuging the cell slurry (crude extract). In the same manner there was obtained a crude extract of Brevibacterium spec. (DSM 2448). The PheDH activity as determined in the two extracts, then there were stored aliquots at 4° C. and at 22° C. and the remaining activity determined at specific times.

Table 6 shows that the storage stability of the PheDH from the strain M4 in the crude extract is clearly better than that of the PheDH from Brevibacterium spec., after 1 week at 4° C. 90% activities are still detectable.

TABLE 6

| Enzyme From | Storage Temperature (°C.) | Remaining Activity After Days (%) | | | |
|---|---|---|---|---|---|
| | | 1 | 2 | 3 | 4 |
| Rhodococcus spec. | 4 | 98 | 93 | 93 | 91 |
| Rhodococcus spec. | 22 | 84 | 74 | 66 | 60 |
| Brevibacterium Spec. | 4 | 70 | 55 | 30 | 20 |

EXAMPLE 7

Production Of L-Phenylalanine With Complete Cells

The sterospecific reaction of phenyl pyruvic acid was also attained using the complete microorganism cells. Incubating under suitable conditions phenyl pyruvic acid, glucose and an ammonium salt with cells of strain M4 there can be detected the formation of phenylalanine, the NADH necessary for the reaction is continuously regenerated by the enzyme/of the glucose metabolism.

Individually, the mixture contained:

| 2 ml NH4Cl-solution pH 7.0 | (200 mM) |
|---|---|
| 3 ml Cell suspension | (0.1 g wet mass per 1 ml) |
| 2 ml Glucose | (200 mM) |
| 1 ml KH2PO4 pH 7.0 | (0.1 M) |
| 2 ml Phenyl pyruvic acid | (50 mM) |

There are given in parentheses the final concentration of the individual components in the test. As source of enzyme there was used a cell suspension of strain M4 which was obtained according to Example 1.

There was incubated besides in comparison a parallel mixture which contained cells of Brevibacterium spec DSM 2448.

The incubations were carried out in 100 ml Erlenmeyer flasks at 30° C. on a shaking machine (100 rpm). Samples were withdrawn at various times and there was determined the content of phenylalanine formed with an aminoacid analyzer.

As is shown in Table 7 the cells of both microorganism are in a position to form phenylalanine:

Strain M4 after 7 hours had formed 36.1 μMole Phe/ml (=53 mg Phe/g bacterial-wet mass); which corresponds to a reaction of 64% of the substrate employed, Brevibacterium spec. (DSM 2448) had formed 18.5 μMol Phe/ml (−46.1 mg PHe/g bacteria wet mass); which corresponds to a reaction of 37% of the phenyl pyruvic acid employed.

TABLE 7

| Strain | Phenylalanine After | | |
|---|---|---|---|
| | 1 h | 3 h | 7 h |
| | (mg/g Cells) | | |
| Rhodococcus spec. | 23 | 35 | 53 |
| Brevibacterium spec. | 15.5 | 27.5 | 46 |

EXAMPLE 8

Production of L-Phenylalanine In The Cell-free system With Regeneration Of NADH

The stereospecific conversion of phenyl pyruvic acid to L-phenylalanine can be carried out in the cell free system. The coenzyme NADH must be added according to the reaction equation. In order to regenerate the coenzyme oxidized in the conversion there was added to the mixture formate-dehydrogenase (E.C. 1.2 1.2) and formate, as additional product there was then obtained $CO_2$.

The mixture contained individually:

400 mM Ammonium formate (pH 9.2)
150 mM Tris-HCl (pH 9.2)
0.3 mM NADH
2 U/ml Formate-Dehydrogenase (preparation according to Kroner et al. (1982), J. Chem. Tech. Biotechnol. 32, 130–137)
2 U/ml Phenylalanine-Dehydrogenase (Preparation having 110 U/mg; Top-Phase according to 1. liquid-liquid distribution according to Tab. 2)
20 mM Phenyl puruvic acid The total volume was 2 ml, the incubation was carried out with stirring at 28° C. The formation of product was followed on the aminoacid analyzer.

Table 8 shows that after 90 minutes 19 mM of product were formed (96% reaction).

TABLE 8

Reaction Of Phenyl Pyruvic Acid To L-Phenylalanine In The Cell-free System (Reaction = Based On The Phenyl Pyruvic Acid Employed

| Time min | L-Phe mM | Reaction % |
| --- | --- | --- |
| 15 | 7.4 | 37 |
| 30 | 12.8 | 64 |
| 60 | 16.8 | 84 |
| 90 | 19.1 | 96 |

The entire disclosure of German priority application P3446304.6 is hereby incorporated by reference.

What is claimed is:

1. A biologically pure culture of Rhodococcus M4, DSM 3041.
2. A biologically pure culture of Rhodococcus 13, DSM 3040.

* * * * *

UNITED STATES PATENT AND TRADEMARK OFFICE
CERTIFICATE OF CORRECTION

PATENT NO. : 5,416,019
DATED : May 16, 1995
INVENTOR(S) : Leuchtenberger et al.

It is certified that error appears in the above-indentified patent and that said Letters Patent is hereby corrected as shown below:

On the title page, item [54], delete "DEHYDROGANASE" and insert therefor --DEHYDROGENASE--.

Signed and Sealed this

Sixteenth Day of July, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.   : 5,416,019
DATED        : May 16, 1995
INVENTOR(S)  : Leuchtenberger, et. al.

It is certified that error appears in the above-indentified patent and that said Letters Patent is hereby corrected as shown below:

Title page, item [73], after "Aktiengesellschaft," insert --Gesellschaft für biotechnologische Forschung mbH--.

Signed and Sealed this

Eleventh Day of March, 1997

Attest:

BRUCE LEHMAN

*Attesting Officer*    Commissioner of Patents and Trademarks